US010499862B2

(12) United States Patent
Ro (10) Patent No.: US 10,499,862 B2
(45) Date of Patent: Dec. 10, 2019

(54) PANORAMIC X-RAY IMAGING APPARATUS

(71) Applicants: VATECH Co., Ltd., Gyeonggi-do (KR); VATECH EWOO Holdings Co., Ltd., Gyeonggi-do (KR)

(72) Inventor: Chang-Joon Ro, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 295 days.

(21) Appl. No.: 15/519,144

(22) PCT Filed: Oct. 13, 2015

(86) PCT No.: PCT/KR2015/010798
§ 371 (c)(1),
(2) Date: Apr. 13, 2017

(87) PCT Pub. No.: WO2016/060449
PCT Pub. Date: Apr. 21, 2016

(65) Prior Publication Data
US 2017/0231582 A1    Aug. 17, 2017

(30) Foreign Application Priority Data

Oct. 13, 2014 (KR) .................... 10-2014-0137312

(51) Int. Cl.
*A61B 6/14* (2006.01)
*A61B 6/00* (2006.01)
(Continued)

(52) U.S. Cl.
CPC ............... *A61B 6/14* (2013.01); *A61B 6/027* (2013.01); *A61B 6/40* (2013.01); *A61B 6/4007* (2013.01);
(Continued)

(58) Field of Classification Search
CPC ......... A61B 6/145; A61B 6/14; Y10S 97/742; Y10S 977/919; Y10S 977/939; Y10S 977/95; B82Y 5/00
See application file for complete search history.

(56) References Cited

U.S. PATENT DOCUMENTS

| 5,214,686 A | 5/1993 | Webber |
|---|---|---|
| 2008/0069420 A1 | 3/2008 | Zhang et al. |

(Continued)

FOREIGN PATENT DOCUMENTS

| JP | 5395958 B2 | 1/2014 |
|---|---|---|
| KR | 10-2014-0008287 A | 1/2014 |
| KR | 10-2014-0106291 A | 9/2014 |

OTHER PUBLICATIONS

Korean Intellectual Property Office, International Search Report of International Application No. PCT/KR2015/010798, dated Jan. 21, 2016.
(Continued)

*Primary Examiner* — Don K Wong
(74) *Attorney, Agent, or Firm* — IP Legal Services, LLC (57) ABSTRACT

The present invention relates to a panoramic X-ray imaging apparatus capable of obtaining more accurate panoramic X-ray images while minimizing the rotation of a rotation arm, the panoramic X-ray imaging apparatus includes at least one X-ray source configured to irradiate X-rays and an X-ray sensor configured to receive the X-rays, a rotating arm configured to position the X-ray sensor and the X-ray source to face each other, a driver configured to rotate the rotating arm about a rotating shaft, a guide configured to provide directions for moving the X-ray sensor or the X-ray source, and wherein the at least one X-ray source is of an electric field emission type adopting an emitter of a nanostructure material and the X-ray source or the X-ray sensor is relatively movable along the guide in conjunction with a movement of the rotating arm.

16 Claims, 7 Drawing Sheets

(51) Int. Cl.
*H01J 35/06* (2006.01)
*H01J 35/08* (2006.01)
*A61B 6/02* (2006.01)

(52) U.S. Cl.
CPC .......... *A61B 6/4021* (2013.01); *A61B 6/4435* (2013.01); *A61B 6/4476* (2013.01); *H01J 35/065* (2013.01); *H01J 35/08* (2013.01); *H01J 2235/068* (2013.01)

(56) References Cited

U.S. PATENT DOCUMENTS

| | | |
|---|---|---|
| 2013/0136226 A1 | 5/2013 | Tomoe et al. |
| 2014/0241498 A1 | 8/2014 | Jeong et al. |
| 2015/0036797 A1* | 2/2015 | Nachaliel ............. A61B 6/4057 378/38 |
| 2015/0305696 A1 | 10/2015 | Yamakawa et al. |

OTHER PUBLICATIONS

Korean Intellectual Property Office, Written Opinion of International Application No. PCT/KR2015/010798, dated Jan. 21, 2016.

* cited by examiner

PANORAMIC X-RAY IMAGING APPARATUS

CROSS REFERENCE TO RELATED APPLICATIONS

This application is a National Stage Patent Application of PCT International Patent Application No. PCT/KR2015/010798 (filed on Oct. 13, 2015) under 35 U.S.C. § 371, which claims priority to Korean Patent Application No. 10-2014-0137312 (filed on Oct. 13, 2014), the teachings of which are incorporated herein in their entireties by reference.

TECHNICAL FIELD

The present invention relates generally to panoramic radiography. More particularly, the present invention relates to a panoramic X-ray imaging apparatus that is capable of obtaining a more accurate panoramic X-ray image while minimizing rotation of a rotating arm.

BACKGROUND ART

An X-ray is an electromagnetic wave having a short wavelength corresponding to a wavelength band of 10 to 0.01 nm and a frequency band of 30×10 15 to 30×10 18 Hz, and shows straightness, penetration, and attenuation that X-ray is attenuated according to an X-ray attenuation coefficient unique to a substance in the process of penetrating through the substance placed in a path of the X-ray.

X-ray radiography is a radiography method using straightness, penetration, and attenuation of X-rays, and based on the amount of attenuation accumulated in the course of the X-rays passing through an FOV (field of view), it displays a gray-level X-ray image of the internal structure of the FOV. To achieve this, an X-ray imaging apparatus includes: an X-ray source configured to irradiate X-rays to an FOV; an X-ray sensor configured to detect X-rays that have penetrated through the FOV; and an image processor configured to reconstruct an X-ray image of an internal structure of the FOV by using X-ray projection data, as a detection result detected by the X-ray sensor.

In recent years, X-ray radiography has been rapidly evolving into DR (Digital Radiography) using digital sensors due to the development of semiconductor and information processing technologies, whereby image processing technology has also been developed and is used in various ways according to the purpose and application field.

Figure 1:
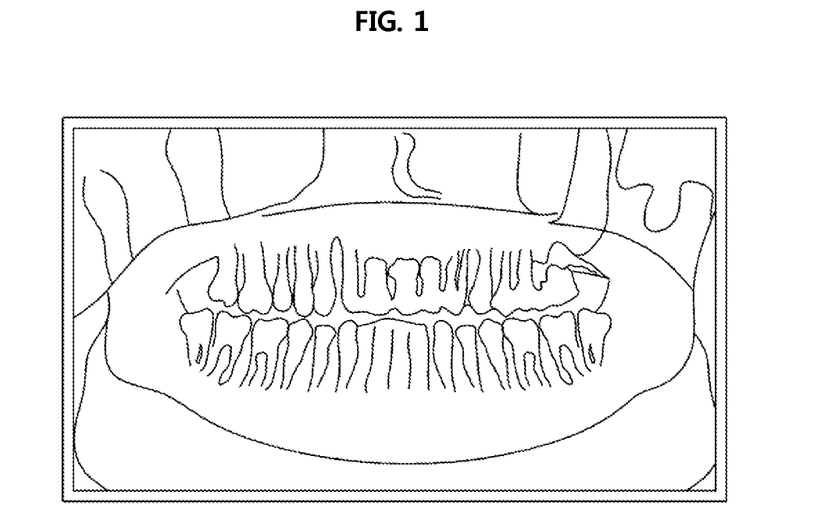
FIG. 1 is a view showing a general panoramic X-ray image.

FIG. 1 shows a panoramic X-ray image that is mainly used in the dental field.

As shown in the drawing, a general panoramic X-ray image displays an arrangement relation between a tooth and tissue therearound of any image layer in the dental arch, as a two-dimensional transmission image. Accordingly, the panoramic X-ray image is used as a standard image most familiar to dentists because it can be used to easily identify the overall arrangement of a tooth and tissue therearound with only a single image.

Further, to obtain the panoramic X-ray image, the focal interval between the X-ray source and the X-ray sensor is shifted along any image layer in the dental arch, thereby acquiring X-ray projection data for each section of the image layer, and the X-ray penetration data is appropriately superimposed on a two-dimensional plane to form a panoramic X-ray image for the image layer.

Figure 2:
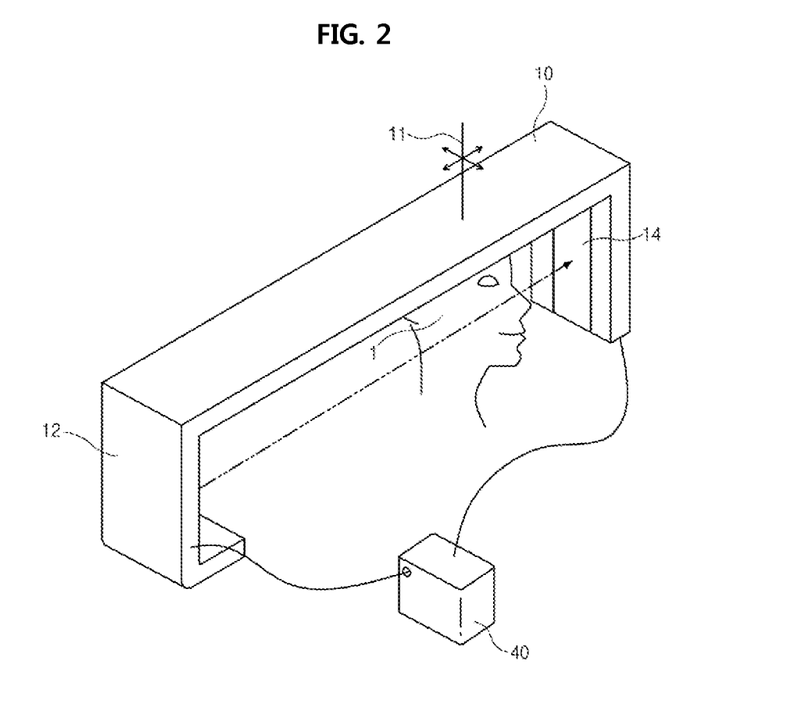
FIG. 2 is a schematic view showing a general panoramic X-ray imaging apparatus.

FIG. 2 is a schematic view showing a general panoramic X-ray imaging apparatus.

As shown in the drawing, a general panoramic X-ray imaging apparatus roughly includes: a radiography unit having an X-ray source 12 and an X-ray sensor 14; and an image processor 40 configured to realize a panoramic X-ray image based on a detection result detected by the X-ray sensor 14. Further, the radiography unit includes: a rotating arm 10 configured to position the X-ray source 12 and the X-ray sensor 14 to face each other with a subject 1 therebetween; and a driver (not shown) configured to rotate and move the rotating arm 10 about a rotating shaft 11 between the X-ray source 12 and the X-ray sensor 14.

Here, the driver of the general panoramic X-ray imaging apparatus is performed by a two-axis drive system, which is configured to rotate the rotating arm 10 about the rotating shaft 11 and linearly move the rotating arm 10 along a plane perpendicular to a longitudinal direction of the rotating shaft, such that the focal interval between the X-ray source 12 and the X-ray sensor 14 is shifted along any image layer in the dental arch.

However, the two-axis drive system of the general panoramic X-ray imaging apparatus has several problems.

For example, for two-axis driving, two or more driving sources, such as a motor, being in cooperation with each other are required, and particularly, for constant superimposition of the X-ray projection data, the shift interval of the X-ray source 12 and the X-ray sensor 14 should be precisely controlled. Due to this, the entire configuration of the apparatus becomes complicated and large, and also, rotation speed, movement speed, and trajectory are limited. Accordingly, the radiography time is lengthened and the amount of radiation applied to the subject is increased, and the possibility of interference such as collision with the subject is always involved.

DISCLOSURE

Technical Problem

Accordingly, the present invention has been made keeping in mind the above problems occurring in the prior art, and an object of the present invention is to provide a panoramic X-ray imaging apparatus that is capable of obtaining a more accurate panoramic X-ray image while minimizing physical positional movement of a rotating arm.

Technical Solution

In order to accomplish the above object, the present invention provides a panoramic X-ray imaging apparatus including: at least one X-ray source configured to irradiate X-rays that penetrate through an image layer within a dental arch from section to section, behind the dental arch; and an X-ray sensor configured to receive the X-rays penetrating through the image layer within the dental arch from section to section, in front of the dental arch, wherein the at least one X-ray source is of an electric field emission type adopting an emitter of a nanostructure material.

Here, preferably, the panoramic X-ray imaging apparatus further includes: a rotating arm configured to position the X-ray sensor and the X-ray source to face each other, with a rotating shaft disposed therebetween; and a driver configured to rotate the rotating arm about the rotating shaft, move the rotating aim along a plane perpendicular to the rotating shaft, or rotate and move the rotating aim.

Further, preferably, the X-ray source is provided two or more in number along left and right directions of the dental arch.

Further, preferably, the panoramic X-ray imaging apparatus further includes a sensor mover configured to move the X-ray sensor with respect to the rotating arm in the left and right directions of the dental arch.

Further, preferably, the panoramic X-ray imaging apparatus further includes a source mover configured to move the X-ray source with respect to the rotating arm in the left and right directions of the dental arch.

Further, preferably, the X-ray source includes: a cathode electrode provided at a first side of a vacuum housing, with the emitter provided on a surface thereof; and an anode electrode provided at a second side of the housing, and configured to provide a target facing the cathode electrode, with the emitter disposed therebetween.

Further, preferably, the panoramic X-ray imaging apparatus further includes a gate electrode provided between the emitter and the target, and configured to control electric field emission of the emitter.

Further, preferably, the panoramic X-ray imaging apparatus further includes a focusing electrode provided between the gate electrode and the target, and configured to focus the electric field on the target.

Advantageous Effects

The present invention provides a panoramic X-ray imaging apparatus, which is capable of obtaining a more accurate panoramic X-ray image by adopting at least one X-ray source while minimizing physical positional movement of a rotating arm.

Particularly, the present invention uses an electric field emission type adopting an emitter of a nanostructure material as an X-ray source, and is configured such that at least one of the X-ray sensor and X-ray source is movable with respect to a rotating arm in the left and right directions of the dental arch, and if necessary, the movement thereof is in conjunction with the rotation of the rotating arm, whereby it is possible to minimize physical positional movement of the rotating arm.

Accordingly, it is possible to obviate the need for large-sized equipment due to unnecessary control elements and the like, and is possible to reduce the possibility of interference such as collision with a subject.

MODE FOR INVENTION

Detailed features and advantages of the present invention will be apparent from the following detailed description based on the accompanying drawings. However, it should be understood that the embodiment of the present invention may be changed to a variety of embodiments and the scope and spirit of the present invention are not limited to the embodiment described hereinbelow. The embodiment of the present invention described hereinbelow is provided for allowing those skilled in the art to more clearly comprehend the present invention.

The terminology used herein is for the purpose of describing particular embodiments only and is not intended to be limiting. As used herein, the singular forms "a", "an", and "the" are intended to include the plural forms as well, unless the context clearly indicates otherwise. It will be further understood that the terms "comprise", "include", "have", etc. when used in this specification, specify the presence of stated features, integers, steps, operations, elements, components, and/or combinations of them but do not preclude the presence or addition of one or more other features, integers, steps, operations, elements, components, and/or combinations thereof.

In the embodiment of the present invention described hereinbelow, the term 'module' or 'unit' means a functional part performing at least one function or action, which may be realized with a hardware or a software, or a combination of a hardware and a software. Further, except 'module' or 'unit' that need to be realized with specific hardware, a plurality of 'modules' or a plurality of 'parts' may be integrated into at least one module to be realized as at least one processor.

In addition, unless otherwise defined, all terms including technical and scientific terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Hereinbelow, preferred embodiments of the present invention will be described in detail with reference to the accompanying drawings. In the following description, it is to be noted that when the functions of conventional elements and the detailed description of elements related with the present invention may make the gist of the present invention unclear a detailed description of those elements will be omitted.

Figure 3:
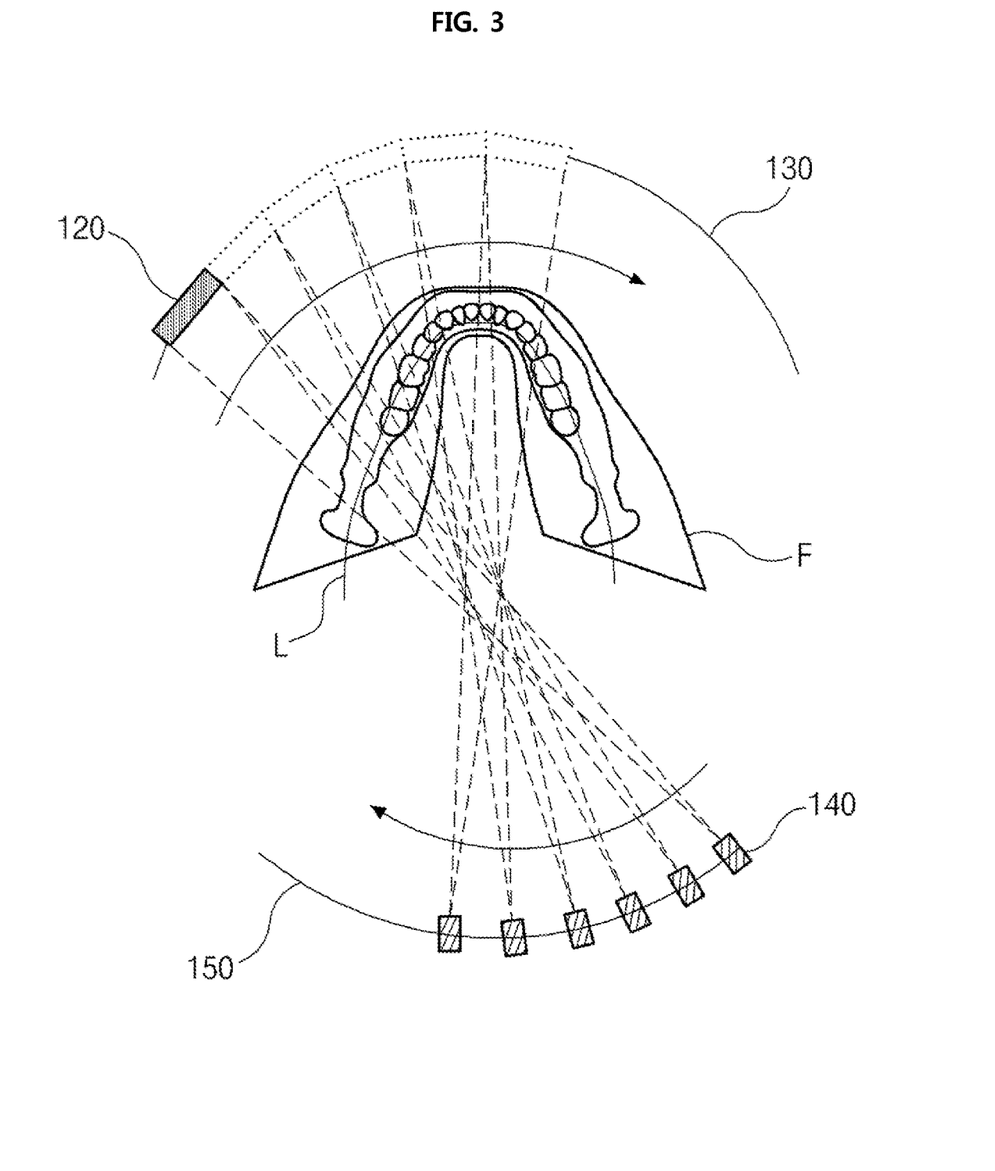
FIG. 3 is a diagram showing imaging principle of a panoramic X-ray image according to the present invention.

FIG. 3 is a diagram showing imaging principle of a panoramic X-ray image according to the present invention.

As shown in the drawing, a panoramic X-ray imaging apparatus according to the present invention essentially includes: an X-ray sensor 120 disposed in front of a field of view, namely, in front of a dental arch F; at least one X-ray source 140 disposed behind the field of view, namely, behind the dental arch F; and an image processor (see reference numeral 40 in FIG. 2, hereinafter the same.) configured to realize a panoramic X-ray image based on a detection result detected by the X-ray sensor 120 although not shown in the drawings, and preferably, the panoramic X-ray imaging apparatus further includes at least one of the following: a sensor mover configured to move the X-ray sensor 120 in the left and right directions of the dental arch F in front of the dental arch F; and a source mover configured to move the at least one X-ray source 140 in the left and right directions of the dental arch F behind the dental arch F.

Detailed description of the above elements is as follows.

The X-ray sensor 120 is configured to respectively receive the X-rays generated by the X-ray source 140 and which have penetrated through the dental arch F, particularly, through any image layer L within the dental arch F from section to section. To achieve this, a direct or indirect CMOS or TFT image sensor having a predetermined height in the vertical direction of the dental arch F and a predetermined width in the lateral direction of the dental arch F may be used as the X-ray sensor 120. For example, a height of the X-ray sensor 120 may be more than a height of the dental arch F with a magnification ratio reflected, and assuming that the minimum unit for distinction of the image layer corresponds to one pixel of the X-ray sensor 120, a width of the X-ray sensor 120 is sufficient to provide an area corresponding to one pixel line or more. However, considering imaging efficiency, the width of the X-ray sensor 120 may be more than that of an X-ray sensor used for a conventional panoramic X-ray imaging.

Here, the X-ray sensor 120 of the panoramic X-ray imaging apparatus according to the present invention is configured to receive the X-rays that have penetrated through any image layer L within the dental arch F from section to section while moving along an incident surface 130 in front of the dental arch F, and to achieve this, the sensor mover physically moves the X-ray sensor 120 along a sensor movement trajectory corresponding to the incident surface 130.

For reference, the incident surface 130 may be in a vertical planar shape or a curved shape that faces the height and width directions of the field of view, wherein the curved incident surface 130 may be in a shape that corresponds to the dental arch F, that is, in an arch or similar shape with the cross section perpendicular to the height direction embracing the dental arch F, or in a reverse shape, that is, in an arch or similar shape with the back thereof turning to the dental arch F. In other words, the shape of the incident surface 130 is not limited to a predetermined shape as long as it can receive X-rays of any image layer L within the dental arch F from section to section at different positions in front of the dental arch F.

Further, the sensor mover physically moves the X-ray sensor 120 along the incident surface 130. Here, specific configuration of the sensor mover may vary, and some examples thereof will be discussed in detail.

As a result, the X-ray sensor 120 may receive X-rays that have penetrated through any image layer L within the dental arch F from section to section while moving along the incident surface 130.

For reference, in the above description, the width of the X-ray sensor 120 is smaller than that of the incident surface 130. On the contrary, if the width of the X-ray sensor 120 is larger than that of the incident surface 130, it is possible to receive the X-rays that have penetrated through any image layer L within the dental arch F from section to section, without physically moving the X-ray sensor 120. In this case, the X-ray sensor 120 may be in a vertical planar shape or a curved shape that corresponds to the incident surface 130.

The X-ray source 140 irradiates X-rays that penetrate through any image layer L within the dental arch F from section to section. To achieve this, the X-ray source 140 may be provided in plural, and each X-ray source 140 may be of an electric field emission type adopting an emitter of a nanostructure material, such as a carbon nanotube.

Figure 4:
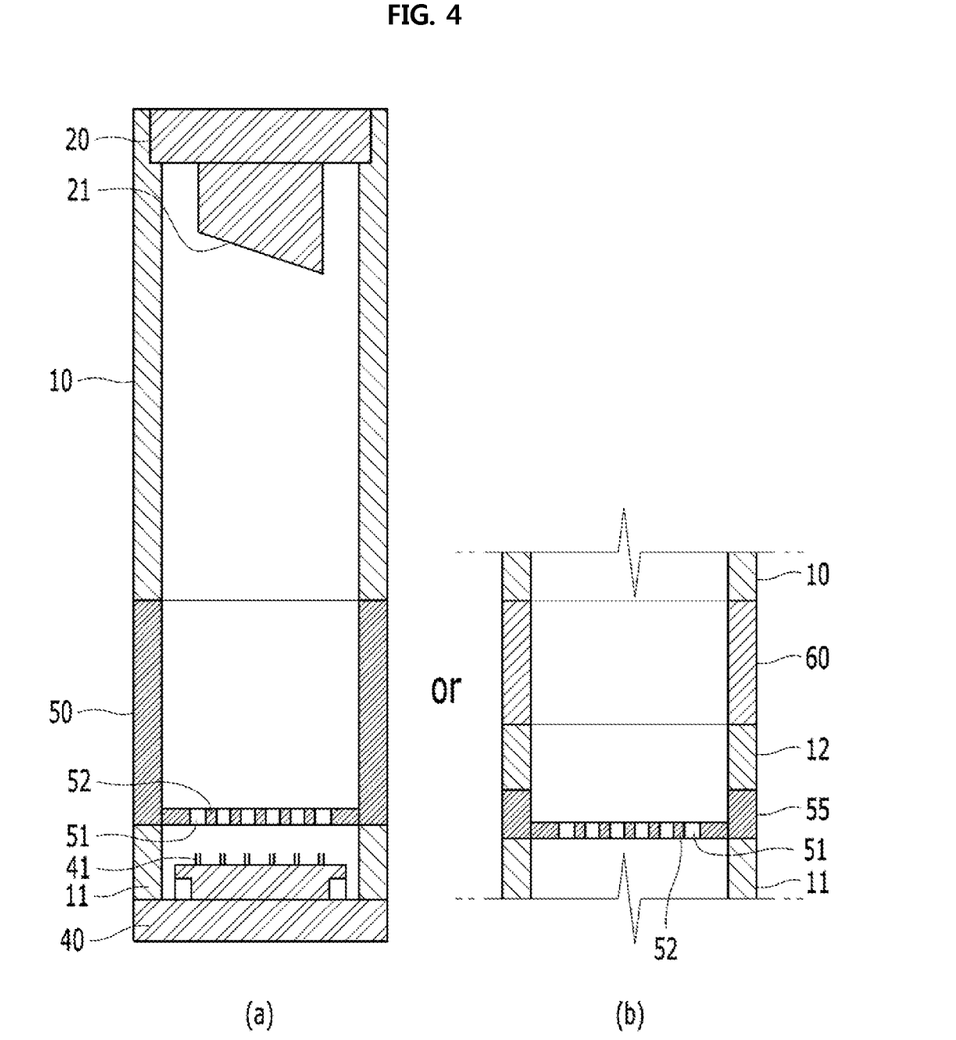
FIG. 4 is a diagram showing sectional views of X-ray sources of a panoramic X-ray imaging apparatus according to the present invention.

FIG. 4 is a diagram showing the X-ray sources of the panoramic X-ray imaging apparatus according to the present invention.

As shown in the drawing, the X-ray source is a part of a tubular housing that forms a vacuum space therein, and includes: an upper insulating spacer 10; an anode electrode 20 disposed at an upper end of the upper insulating spacer 10; a gate electrode 50 attached to a lower end of the upper insulating spacer 10; and a cathode electrode 40 disposed at lower end of a lower insulating spacer 11 as the rest part of the housing.

An electron emission source 41 is provided on the cathode electrode 40, wherein the electron emission source 41 may be provided in an additional substrate (not shown) so as to be connected to the cathode electrode 40, or in some cases, it may be formed directly on the cathode electrode 40. The electron emission source 41 may be, for example, of a plurality of nanostructure materials, such as a carbon nanotube. In the case of the electron emission source 41 adopting the carbon nanotube, a plurality of carbon nanotubes may be grown directly on the substrate or on the cathode electrode 40 by chemical vapor deposition (CVD), or may be provided by plastic deformation after applying a carbon nanotube paste on the substrate or on the cathode electrode.

The gate electrode 50 may be configured, for example, as shown in left view (a), to be provided with a horizontal electrode portion 52 having a plurality of gate holes 51, wherein a main body of the gate electrode is connected directly to the horizontal electrode portion 52 and extends in a longitudinal direction of the upper insulating spacer 10. The horizontal electrode portion 52 is configured to form an electric field that starts and controls electron emission, by being disposed close to the electron emission source 41, and it may be in the form of a thin metal plate or a metal mesh that is formed with a plurality of gate holes 51 so as to allow an electron beam E to pass therethrough.

As described above, the gate electrode 50 that has a part extending in the longitudinal direction of the upper insulating spacer 10 may also serve as a so-called focusing electrode that is configured such that an equipotential surface of the main body forms an inclined electric field inclined toward the center of the anode electrode 20 and focuses the proceeding electron beam on the center.

The upper insulating spacer 10 and the lower insulating spacer 11 may be made of an insulating material, such as ceramic, glass, silicon, or the like, and for example, may be made of alumina ceramics. As the upper and lower insulating spacers 10 and 11 are made of an insulating material, the field emission X-ray source is configured such that the anode electrode 20, the cathode electrode 40, and the gate electrode 50 are electrically insulated from each other. Meanwhile, the X-ray source, as shown in right view (b), may include: a gate electrode 55 having a plurality of gate holes 51 and a horizontal electrode portion 52; and an additional focusing electrode 60 with a middle insulating spacer 12 disposed between the gate electrode and the focusing electrode.

The anode electrode 20 serves as an accelerating electrode by forming a high potential difference of several tens to hundreds of kV from the cathode electrode 40 in which the electron emission source 41 is disposed, and simultaneously serves as an X-ray target that emits X-rays by collision of accelerated electrons emitted from the electron emission source 41. To achieve this, the anode electrode 20 is disposed to face the inside of the upper insulating spacer 10, and has an X-ray target surface 21 slanted obliquely with respect to a progressing direction of the electron beam E.

An additional target member may be provided in the X-ray target surface 21. The target member may be made of tungsten (W), copper (Cu), molybdenum (Mo), cobalt (Co), chromium (Cr), iron (Fe), silver (Ag), tantalum (Ta), or yttrium (Y) that emits X-rays by bombardment of the accelerated electron beam E, wherein Tungsten (W) having high melting point and excellent X-ray emission efficiency is mainly applied.

When compared to a conventional hot cathode X-ray source apparatus, the above described small sized X-ray source is capable of emitting electrons by applying a low voltage, and since electrons to be emitted are emitted along a longitudinal direction of the carbon nanotube, the electrons have good directivity toward a target of an anode electrode, so efficiency in X-ray emission is very high. Further, since it is easy to emit X-rays in a pulse shape, it is possible to obtain an X-ray image with a low dose of X-ray radiation.

Referring back to FIG. 3, the at least one X-ray source 140 generates X-rays that penetrate through any image layer L within the dental arch F from section to section, behind the dental arch F. Here, particularly, the X-ray source 140 may be provided in plural and be movable along a predetermined trajectory toward the left and right directions of the dental arch F, and in this case, the source mover physically moves the at least one X-ray source 140 along a predetermined source trajectory 150.

As a result, the at least one X-ray source 140 is capable of generating X-rays that penetrate through any image layer L within the dental arch F from section to section.

Figure 5:
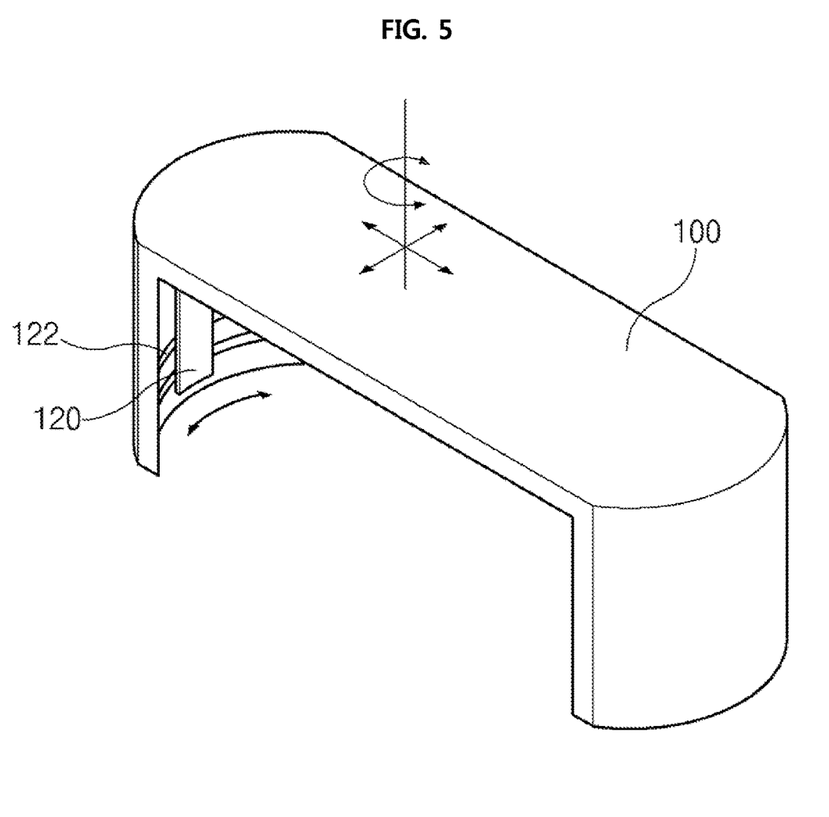
FIG. 5 is a schematic view showing the panoramic X-ray imaging apparatus.

FIG. 5 is a schematic view showing an example of the panoramic X-ray imaging apparatus.

As shown in the drawing, the panoramic X-ray imaging apparatus according to the present invention may include a rotating arm 100 with the X-ray sensor 120 and the X-ray source (see reference numeral 140 in FIG. 3, hereinafter the same.) positioned to opposite ends thereof. Further, the rotating arm 100 may be rotatable about a rotating shaft disposed between the X-ray sensor 120 and the X-ray source 140 and/or movable by the driver that is not shown, wherein the X-ray sensor 120 is disposed at a first end of the rotating arm 100, and the X-ray source 140 is disposed at a second end of the rotating arm 100.

Here, preferably, the X-ray sensor 120 is movable with respect to the rotating arm 100 along the left and right directions of the dental arch by the sensor mover, and to achieve this, the sensor mover, as an example, includes: an LM guide 122 provided at the first end of the rotating arm 100 along the left and right directions of the dental arch; and a linear motor configured to move the X-ray sensor 120 along the LM guide.

As a result, the rotation and/or movement of the rotating arm 100, and the X-ray sensor 120 that is moved by the sensor mover are movable along the incident surface.

Further, preferably, the X-ray source 140 is fixedly provided at the second end of the rotating arm 100 or is movable along the left and right directions of the dental arch by the source mover, and to achieve this, the source mover, as an example, includes: an LM guide provided at the second end of the rotating arm 100 along the left and right directions of the dental arch; and a linear motor configured to move the at least one X-ray source 140 along the LM guide. Here, if necessary, the source mover is capable of moving the at least one X-ray source 140 individually or together.

Meanwhile, the sensor mover and source mover of the panoramic X-ray imaging apparatus according to the present invention are capable of several embodiments in accordance with specific configurations and operations, and reference will be made to each embodiment, hereinafter.

Figure 6:
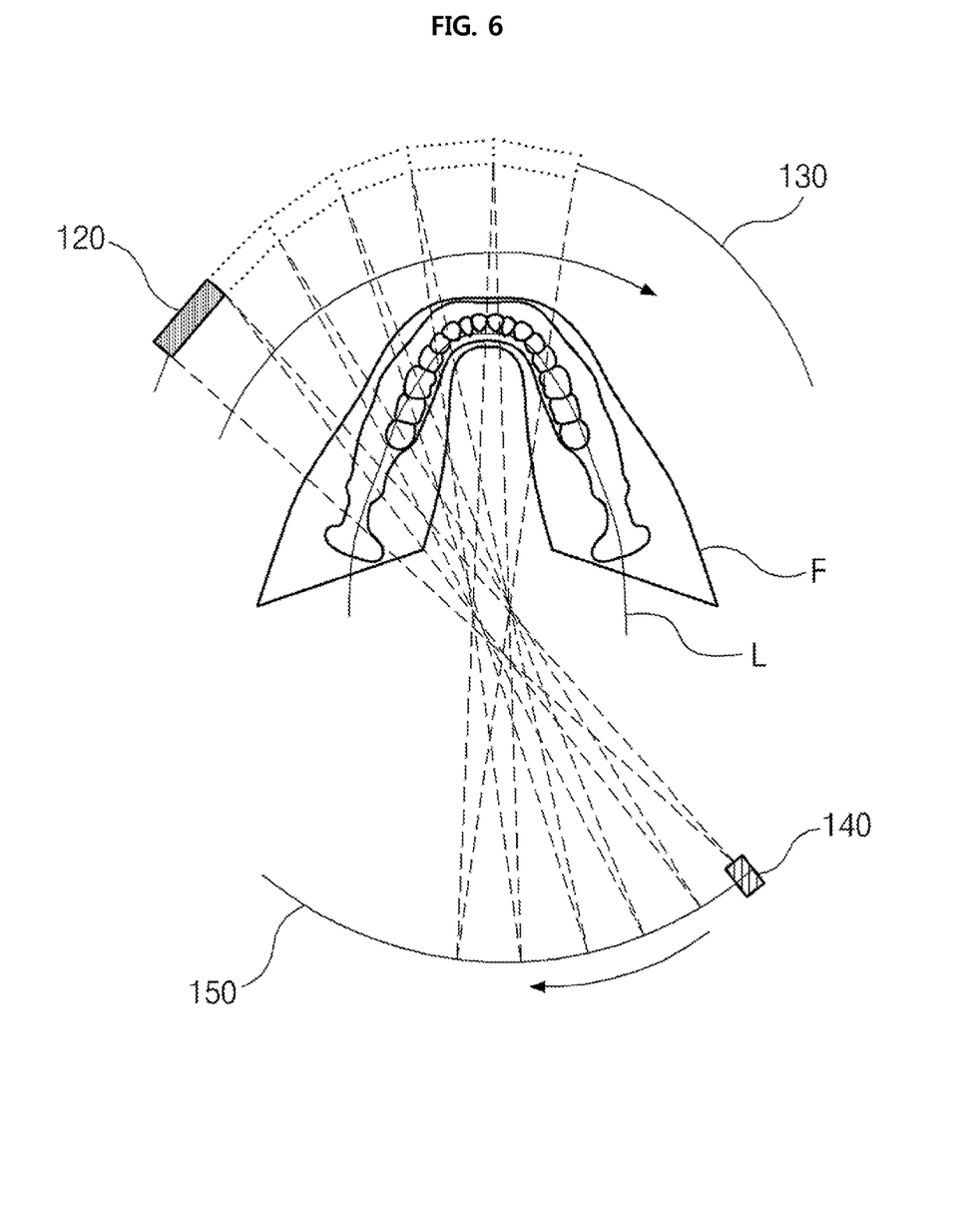
FIGS. 6 to 8 are diagrams showing imaging principle of a panoramic X-ray image according to first to third embodiments of the present invention.

FIG. 6 is a schematic view showing the panoramic X-ray imaging apparatus according to a first embodiment of the present invention. For reference, this figure shows the relative movement between the X-ray sensor 120 and the X-ray source 140 by both the sensor mover and the source mover, and the relative movement may be in conjunction with the rotation and movement of the rotating arm (see reference numeral 110 in FIG. 5, hereinafter the same).

As shown in the drawing, the panoramic X-ray imaging apparatus according to the embodiment is characterized in that a panoramic X-ray image is radiographed by adopting one X-ray source 140.

Further, to achieve this, the sensor mover moves the X-ray sensor 120 in the left and right directions of the dental arch F, for example, from the left to the right, and at the same time, the source mover moves the X-ray source 140 in the left and right directions of the dental arch F, for example, from the right to the left, thereby obtaining X-ray projection images by sections of the entire image layer L within the dental arch F.

Here, particularly, both the movement of the X-ray sensor 120 by the sensor mover and the movement of the X-ray source 140 by the source mover may be in conjunction with the rotation and movement of the rotating arm 110, and through this, it is possible to sufficiently acquire X-ray projection data being in constant superimposition for realizing the panoramic X-ray image.

Figure 7:
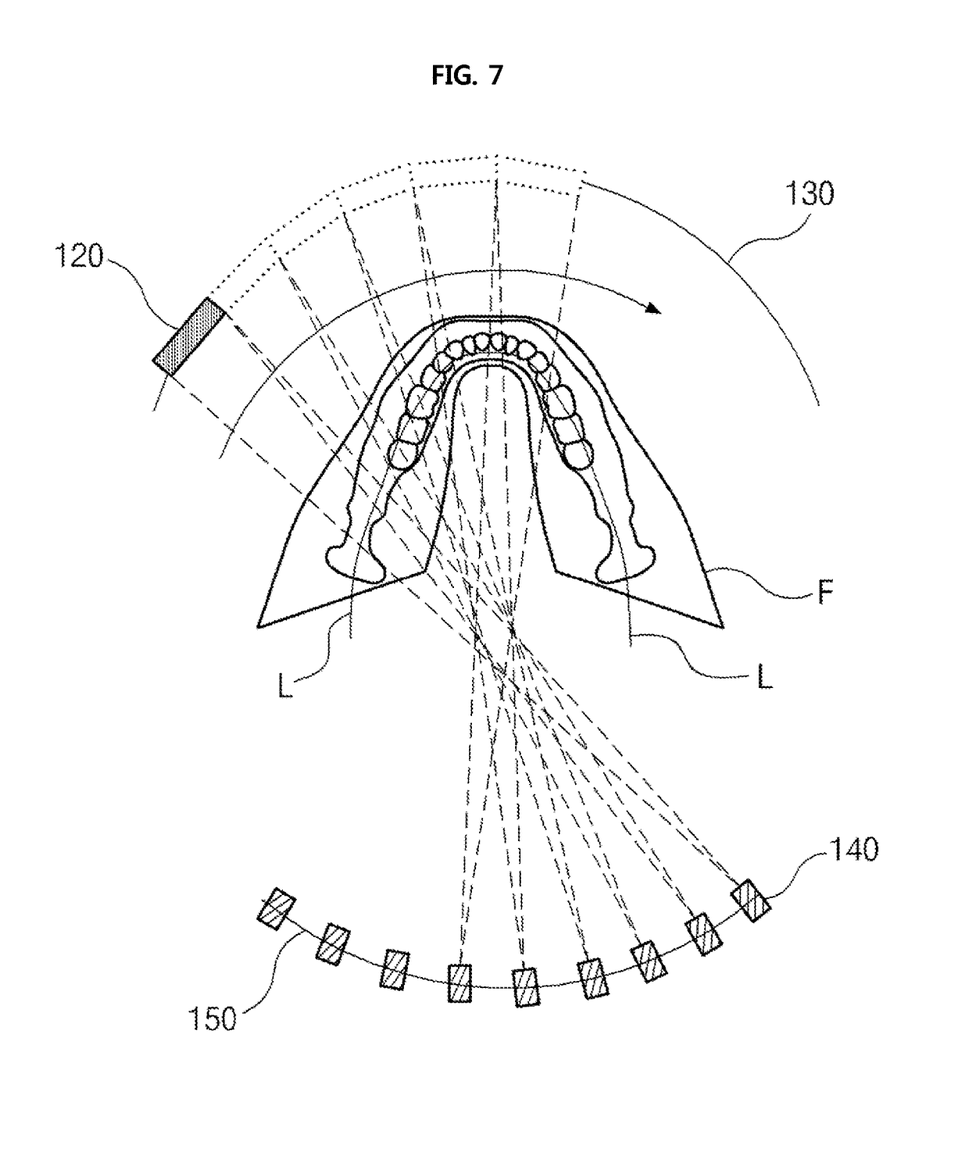

Next, FIG. 7 is a schematic view showing the panoramic X-ray imaging apparatus according to a second embodiment of the present invention. For reference, this figure also shows the relative movement between the X-ray sensor 120 and the X-ray source 140 by both the sensor mover and the source mover, and the relative movement may be in conjunction with the rotation and movement of the rotating arm 110.

As shown in the drawing, the panoramic X-ray imaging apparatus according to the embodiment is characterized in that a panoramic X-ray image is radiographed by adopting a plurality of X-ray sources 140.

Further, to achieve this, the sensor mover moves the X-ray sensor 120 in the left and right directions of the dental arch F, for example, from the left to the right, and at the same time, a plurality of X-ray sources 140 is sequentially driven in the left and right directions of the dental arch F, for example, from the right to the left, thereby obtaining X-ray projection images by sections of the entire image layer L within the dental arch F. For reference, in the embodiment, the source mover may not perform a particular function.

Further, particularly, both the movement of the X-ray sensor 120 by the sensor mover and the sequential driving of a plurality of X-ray sources 140 may be in conjunction with the rotation and movement of the rotating arm 110, and through this, it is possible to sufficiently acquire X-ray projection data being in constant superimposition for realizing the panoramic X-ray image.

Figure 8:
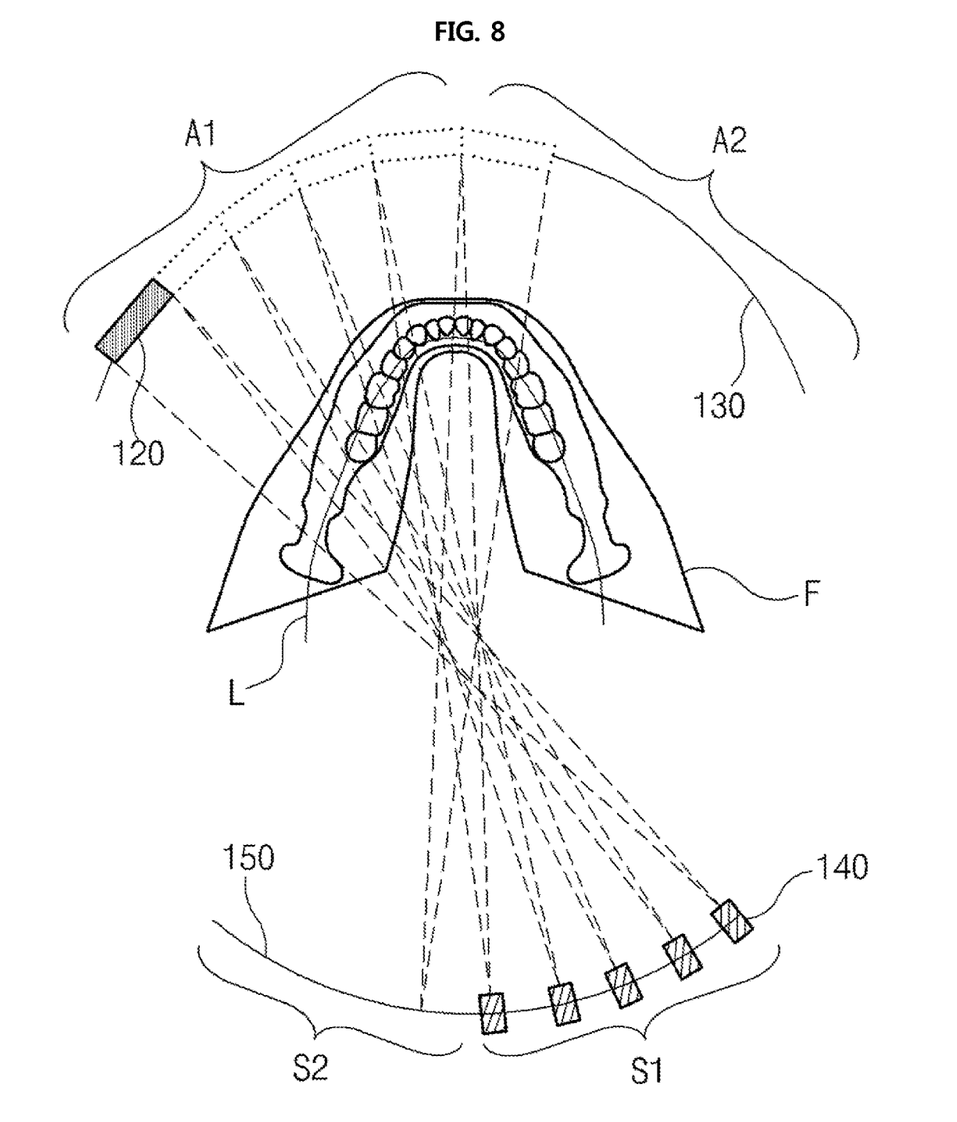

Finally, FIG. 8 is a schematic view showing the panoramic X-ray imaging apparatus according to a third embodiment of the present invention. For reference, this figure shows the relative movement between the X-ray sensor and the X-ray source by both the sensor mover and the source mover, and further shows a conjunction relationship with the rotation of the rotating arm 110, and for convenience, it is assumed that the rotating arm moves from a first position to a second position. Referring to the embodiment, it is easy to predict the conjunction relationship in the first and second embodiments.

As shown in the drawing, the panoramic X-ray imaging apparatus according to the embodiment is characterized in that a panoramic X-ray image is radiographed by adopting a plurality of X-ray sources 140.

Further, to achieve this, the sensor mover moves the X-ray sensor 120 in the left and right directions of the dental arch F at the first position of the rotating arm 110, for example, from the left to the right within section A1, and at the same time, a plurality of X-ray sources 140 is sequentially driven in the left and right directions of the dental arch F, for example, from the right to the left within section S1. Next, the rotating arm 110 rotates toward the second position, and the sensor mover moves the X-ray sensor 120 in the left and right directions of the dental arch F at the second position of the rotating arm 110, for example, from the left to the right within section A2, and at the same time, a plurality of X-ray sources 140 is sequentially driven in the left and right directions of the dental arch F, for example, from the right to the left within section S2.

As a result, X-ray projection images by sections of the entire image layer L within the dental arch F are obtained.

For reference, when the embodiment is compared to the second embodiment, even though the movement interval of the X-ray sensor 120 by the sensor mover and the quantity of the X-ray source 140 are limited, it is possible to sufficiently acquire X-ray projection data being in constant superimposition for realizing the panoramic X-ray image through the rotation of the rotating arm 110. Further, referring to this, in the first embodiment, in the case of being in conjunction with the rotation of the rotating aim 110, it is possible to sufficiently acquire X-ray projection data being in constant superimposition for realizing the panoramic X-ray image even though the movement interval of the X-ray sensor 120 by the sensor mover and the movement interval of the X-ray source 140 by the source mover are limited.

The invention claimed is:

1. A panoramic X-ray imaging apparatus comprising:
   at least one X-ray source configured to irradiate X-rays to an object;
   an X-ray sensor configured to receive the X-rays having passed the object;
   a rotating arm configured to position the X-ray sensor and the X-ray source to face each other;
   a driver configured to rotate the rotating arm about a rotating shaft;
   a guide configured to provide directions for moving the X-ray sensor or the X-ray source; and
   wherein the at least one X-ray source is of an electric field emission type, and
   wherein the at least one X-ray source is provided two or more in number along left and right directions of a dental arch, and
   wherein the X-ray source or the X-ray sensor is relatively movable along the guide in conjunction with a movement of the rotating arm.

2. The panoramic X-ray imaging apparatus of claim 1, wherein the guide is configured to direct the X-ray sensor or the X-ray source in association with the dental arch.

3. The panoramic X-ray imaging apparatus of claim 1, further comprising:
   a sensor mover including a linear motor and configured to move the X-ray sensor with respect to the rotating arm by the linear motor.

4. The panoramic X-ray imaging apparatus of claim 3, further comprising:
   a source mover including a linear motor and configured to move the X-ray source with respect to the rotating arm by the linear motor.

5. The panoramic X-ray imaging apparatus of claim 1, wherein the X-ray source includes:
   a cathode electrode provided at a first side of a vacuum housing, with the emitter provided on a surface thereof; and
   an anode electrode provided at a second side of the housing, and configured to provide a target facing the cathode electrode, with the emitter disposed therebetween.

6. The panoramic X-ray imaging apparatus of claim 5, further comprising:
   a gate electrode provided between the emitter and the target, and configured to control electric field emission of the emitter.

7. The panoramic X-ray imaging apparatus of claim 6, further comprising:
   a focusing electrode provided between the gate electrode and the target, and configured to focus the electric field on the target.

8. The panoramic X-ray imaging apparatus of claim 1, wherein the X-ray sensor or the X-ray source moves while the rotating arm moves.

9. A panoramic X-ray imaging apparatus comprising:
   a plurality of X-ray sources configured to irradiate X-rays to an object;
   an X-ray sensor configured to receive the X-rays having passed the object;
   a rotating arm configured to position the X-ray sensor and the X-ray source to face each other;
   a driver configured to rotate the rotating arm about a rotating shaft;
   a guide configured to provide directions for moving the X-ray sensor or the X-ray source; and
   wherein the at least one X-ray source is of an electric field emission type, and
   wherein the plurality of X-ray sources are sequentially driven along with a movement of the X-ray sensor along the guide.

10. The panoramic X-ray imaging apparatus of claim 9, further comprising:
    a sensor mover including a linear motor and configured to move the X-ray sensor with respect to the rotating arm by the linear motor.

11. The panoramic X-ray imaging apparatus of claim 9, further comprising:
    a source mover including a linear motor and configured to move the X-ray source with respect to the rotating arm by the linear motor.

12. The panoramic X-ray imaging apparatus of claim 9, wherein the X-ray sensor or the X-ray source moves while the rotating arm moves.

13. A panoramic X-ray imaging apparatus comprising:
    a plurality of X-ray sources configured to irradiate X-rays to an object;
    an X-ray sensor configured to receive the X-rays having passed the object;
    a rotating arm configured to position the X-ray sensor and the X-ray source to face each other;
    a driver configured to rotate the rotating arm about a rotating shaft;
    a guide configured to provide directions for moving the X-ray sensor or the X-ray source; and
    wherein the at least one X-ray source is of an electric field emission type, and
    wherein the plurality of X-ray sources are sequentially driven at positions of the rotating arm.

14. The panoramic X-ray imaging apparatus of claim 13, further comprising:

a sensor mover including a linear motor and configured to move the X-ray sensor with respect to the rotating arm by the linear motor.

15. The panoramic X-ray imaging apparatus of claim 13, further comprising:

a source mover including a linear motor and configured to move the X-ray source with respect to the rotating arm by the linear motor.

16. The panoramic X-ray imaging apparatus of claim 13, wherein the X-ray sensor or the X-ray source moves while the rotating arm moves.

* * * * *